(12) United States Patent
Old

(10) Patent No.: US 8,440,819 B2
(45) Date of Patent: May 14, 2013

(54) THERAPEUTIC SUBSTITUTED BETA-LACTAMS

(75) Inventor: David W. Old, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 339 days.

(21) Appl. No.: 12/372,417

(22) Filed: Feb. 17, 2009

(65) Prior Publication Data

US 2009/0215740 A1     Aug. 27, 2009

Related U.S. Application Data

(60) Provisional application No. 61/030,676, filed on Feb. 22, 2008.

(51) Int. Cl.
*C07D 205/08*  (2006.01)
*A61K 31/397*  (2006.01)
*A61P 17/14*   (2006.01)
*A61P 27/06*   (2006.01)

(52) U.S. Cl.
USPC ............................................. 540/200

(58) Field of Classification Search ............ 514/210.02; 540/200
See application file for complete search history.

(56) References Cited

U.S. PATENT DOCUMENTS

| | | | | |
|---|---|---|---|---|
| 3,943,123 | A * | 3/1976 | Bose | 540/200 |
| 7,091,231 | B2 | 8/2006 | Donde | |
| 7,674,786 | B2 * | 3/2010 | Old et al. | 514/210.02 |
| 2006/0252742 | A1 | 11/2006 | Old | |
| 2007/0287742 | A1 | 12/2007 | Old | |
| 2009/0186866 | A1 * | 7/2009 | Old et al. | 514/210.02 |
| 2009/0227557 | A1 * | 9/2009 | Old | 514/210.02 |
| 2009/0318404 | A1 * | 12/2009 | Old | 514/210.02 |

FOREIGN PATENT DOCUMENTS

| | | |
|---|---|---|
| EP | 0 337 549 | 10/1989 |
| WO | WO 2006/098918 | 9/2006 |
| WO | WO 2006/121708 | 11/2006 |
| WO | WO 2006/121822 | 11/2006 |
| WO | WO 2008/021975 | 2/2008 |

OTHER PUBLICATIONS

H.S. Patel, V.K. Patel: Synthesis of Some New N-(4-(N,N'-dimethylaminosulfonylphenyl)-3-chloro-4-phenyl azetidine-2-ones, Indian Journal of Heterocyclic Chemistry, vol. 12, No. 3, 2003, pp. 253-256.
Silverman, Richard B.: Prodrugs and Drug Delivery Systems, Organic Chemistry of Drug Design and Drug Action, 2d Ed., Elsevier Academic Press: Amsterdam, 2004, pp. 496-557.

* cited by examiner

*Primary Examiner* — Mark Berch
(74) *Attorney, Agent, or Firm* — Kevin J. Forrestal

(57) ABSTRACT

A compound having a structure

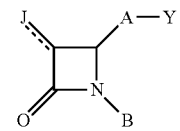

or a pharmaceutically acceptable salt thereof, or a prodrug thereof;
wherein a dashed line represents the presence or absence of a bond;
Y has from 0 to 14 carbon atoms and is: an organic acid functional group, or an amide or ester thereof; hydroxymethyl or an ether thereof; or a tetrazolyl functional group;
A is —$(CH_2)_6$—, cis-$CH_2CH=CH-(CH_2)_3$—, or —$CH_2C\equiv C-(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1 -$CH_2$— may be replaced by S or O, and 1 -$CH_2$—$CH_2$— may be replaced by —CH=CH— or —C≡C—;
J is hydrogen, OH, O, SH, S, $C_{1-6}$ alkyl, —O—($C_{1-6}$ alkyl), —S—($C_{1-6}$ alkyl), F, Cl, Br, I, CN, or $CF_3$; and
B is aryl or heteroaryl,
is disclosed herein. Therapeutic methods, compositions, and medicaments related thereto are also disclosed.

3 Claims, No Drawings

THERAPEUTIC SUBSTITUTED BETA-LACTAMS

RELATED APPLICATION

This application claims the benefit of U.S. Provisional Application Ser. No. 61/030,676, filed Feb. 22, 2008, the disclosure of which is hereby incorporated in its entirety herein by reference.

DESCRIPTION OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract. Glaucoma occurs in about 2% of all persons over the age of 40 and may be asymptotic for years before progressing to rapid loss of vision.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

In cases where surgery is not indicated, prostaglandins and prostamides have recently become the first line treatments of glaucoma Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

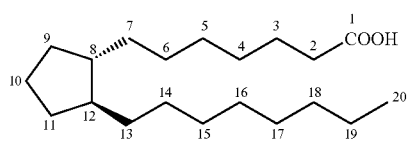

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Disclosed herein is a compound having a structure

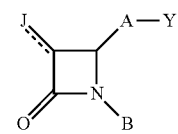

or a pharmaceutically acceptable salt thereof, or a prodrug thereof;

wherein a dashed line represents the presence or absence of a bond;

Y has from 0 to 14 carbon atoms and is: an organic acid functional group, or an amide or ester thereof; hydroxymethyl or an ether thereof; or a tetrazolyl functional group;

A is $-(CH_2)_6-$, cis $-CH_2CH=CH-(CH_2)_3-$, or $-CH_2C\equiv C-(CH_2)_3-$, wherein 1 or 2 atoms may be replaced by S or O; or A is $-(CH_2)_m-Ar-(CH_2)_o-$ wherein Ar is interarylene or heterointerarylene, the sum of m and o is 1, 2, 3, or 4, and wherein $1-CH_2-$ may be replaced by S or O, and $1-CH_2-CH_2-$ may be replaced by $-CH=CH-$ or $-C\equiv C-$;

J is hydrogen, OH, O, SH, S, $C_{1-6}$ alkyl, $-O-(C_{1-6}$ alkyl), $-S-(C_{1-6}$ alkyl), F, Cl, Br, I, CN, or $CF_3$; and B is aryl or heteroaryl.

These compounds are useful for reducing intraocular pressure. Reduction of intraocular pressure has been shown to delay or prevent the onset of primary open angle glaucoma, and to delay or prevent further vision loss in patients with primary open angle glaucoma. Thus, these compounds are also useful for treating glaucoma.

These compounds are also useful for growing hair, including one or more of: increasing the number of individual hairs, increasing the length of individual hairs, and increasing the width or thickness of individual hairs. These compounds are also useful for improving the appearance of hair, including increasing its gloss, shine, or other properties related to the reflection or dispersion of light, as well as changing the color of hair, including changing hair from grey or white to the color the hair was before it turned grey or white, such as red, brown, or black.

Different types of suitable dosage forms and medicaments are well known in the art, and can be readily adapted for delivery of the compounds disclosed herein. For example, the compound could be dissolved or suspended in an aqueous solution or emulsion that is buffered to an appropriate pH, and administered topically to an eye of a mammal (see U.S. Pat. No. 7,091,231).

For the purposes of this disclosure, "treat," "treating," or "treatment" refer to the use of a compound, composition, therapeutically active agent, or drug in the diagnosis, cure, mitigation, treatment, or prevention of disease or other undesirable condition.

Unless otherwise indicated, reference to a compound should be construed broadly to include compounds, pharmaceutically acceptable salts, prodrugs, tautomers, alternate solid forms, non-covalent complexes, and combinations thereof, of a chemical entity of a depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acid/carboxylate), one or more protonated basic groups (e.g. amine/ammonium), or both (e.g. zwitterions).

A prodrug is a compound which is converted to a therapeutically active compound after administration. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject. In particular, alkyl esters having such as methyl, ethyl, isopropyl, and the like are contemplated. Also contemplated are prodrugs containing a polar group such as hydroxyl or morpholine. Examples of such prodrugs include compounds containing the moieties —$CO_2(CH_2)_2OH$,

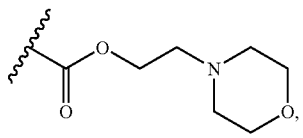

and the like.

Tautomers are isomers that are in rapid equilibrium with one another. For example, tautomers may be related by transfer of a proton, hydrogen atom, or hydride ion.

Unless stereochemistry is explicitly and unambiguously depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

Y is an organic acid functional group, or an amide or ester thereof; or Y is hydroxymethyl or an ether thereof; or Y is a tetrazolyl functional group. For the purposes of this disclosure, Y is limited to from 0 to 14 carbon atoms, from 0 to 5 oxygen atoms, from 0 to 2 nitrogen atoms, from 0 to 2 sulfur atoms, from 0 to 1 phosphorous, and any necessary hydrogen atoms.

An organic acid functional group is an acidic functional group on an organic molecule. While not intending to be limiting, organic acid functional groups may comprise an oxide of carbon, sulfur, or phosphorous. Thus, while not intending to limit the scope of the invention in any way, in certain compounds Y is a carboxylic acid, sulfonic acid, or phosphonic acid functional group.

Amides and esters have the meaning ordinarily understood in the art. For example, esters of amides of carboxylic acid, sulfonic acid, and phosphonic acid functional groups are depicted below.

Acids

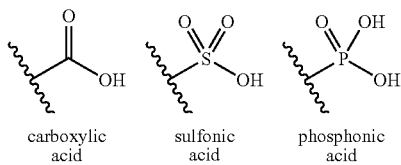

carboxylic acid · sulfonic acid · phosphonic acid

Esters

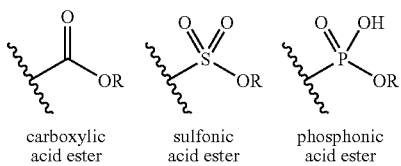

carboxylic acid ester · sulfonic acid ester · phosphonic acid ester

Amides

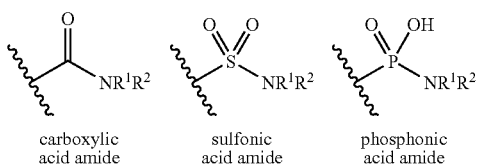

carboxylic acid amide · sulfonic acid amide · phosphonic acid amide

An amide may also have an —$SO_2$— moiety. For example the amide —$CONHSO_2R^3$, wherein $R^3$ is a hydrocarbyl of from 1 to 14 carbon atoms, is contemplated. R, $R^1$, $R^2$, and $R^3$ are hydrocarbyl subject to the constraint that Y may not have more than 14 carbon atoms.

Hydrocarbyl is a moiety consisting of carbon and hydrogen, including, but not limited to:

a. alkyl, which is hydrocarbyl that contains no double or triple bonds, such as:
 linear alkyl, e.g. methyl, ethyl, n-propyl, n-butyl, n-pentyl, n-hexyl, etc.,
 branched alkyl, e.g. isopropyl, t-butyl and other branched butyl isomers, branched pentyl isomers, etc.,
 cycloalkyl, e.g. cyclopropyl, cyclobutyl, cyclopentyl, cyclohexyl, etc.,
 combinations of linear, branched, and/or cycloalkyl;
b. alkenyl, which is hydrocarbyl having 1 or more double bonds, including linear, branched, or cycloalkenyl;
c. alkynyl, which is hydrocarbyl having 1 or more triple bonds, including linear, branched, or cycloalkynyl;
d. unsubstituted or hydrocarbyl substituted phenyl; and
e. combinations of alkyl, alkenyl, and/or akynyl $C_{1-6}$ hydrocarbyl is hydrocarbyl having 1, 2, 3, 4, 5, or 6 carbon atoms.

$C_{1-6}$ alkyl is alkyl having 1, 2, 3, 4, 5, or 6, carbon atoms such as methyl, ethyl, propyl isomers, butyl isomers, pentyl isomer, and hexyl isomers, etc.

Hydroxymethyl is —$CH_2OH$. An ether of hydroxymethyl is —$CH_2O$-hydrocarbyl.

An unsubstituted tetrazolyl functional group has two tautomeric forms, which can rapidly interconvert in aqueous or biological media, and are thus equivalent to one another. These tautomers are shown below.

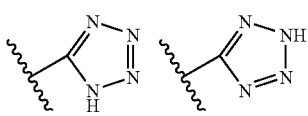

Additionally, if $R^2$ is $C_1$-$C_6$ alkyl, phenyl, or biphenyl, other isomeric forms of the tetrazolyl functional group such as the one shown below are also possible, unsubstituted and hydrocarbyl substituted tetrazolyl up to $C_{14}$ are considered to be within the scope of the term "tetrazolyl."

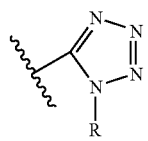

In one embodiment, Y is $—CO_2R^4$, $—CONR^5R^6$, $—CON(CH_2CH_2OH)_2$, $—CONH(CH_2CH_2OH)$, $—CH_2OH$, $—P(O)(OH)_2$, $—CONHSO_2R^4$, $—SO_2NR^5R^6$,

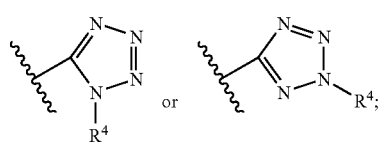

wherein $R^4$, $R^5$ and $R^6$ are independently H, $C_1$-$C_6$ alkyl, $C_{1-6}$ hydroxyalkyl, unsubstituted phenyl, or unsubstituted biphenyl, provided that Y has no more than 14 carbon atoms.

A is $—(CH_2)_6—$, cis $—CH_2CH=CH—(CH_2)_3—$, or $—CH_2C\equiv C—(CH_2)_3—$, wherein 1 or 2 carbon atoms may be replaced by S or O; or A is $—(CH_2)_m—Ar—(CH_2)_o—$ wherein Ar is interarylene or heterointerarylene, the sum of m and o is 1, 2, 3, or 4, and wherein 1 $—CH_2—$ may be replaced by S or O, and 1 $—CH_2—CH_2—$ may be replaced by $—CH=CH—$ or $—C\equiv C—$.

Thus, A may be $—(CH_2)_6—$, cis $—CH_2CH=CH—(CH_2)_3—$, or $—CH_2C\equiv C—(CH_2)_3—$.

Alternatively, A may be a group which is related to one of these three moieties in that any carbon is replaced with S or O. For example, A may be a moiety where S replaces one or two carbon atoms such as one of the following or the like.

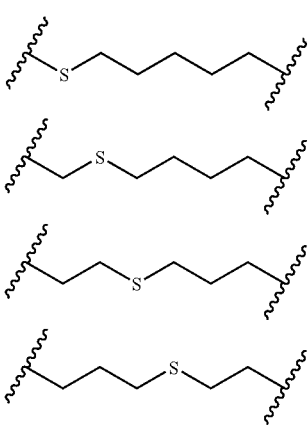

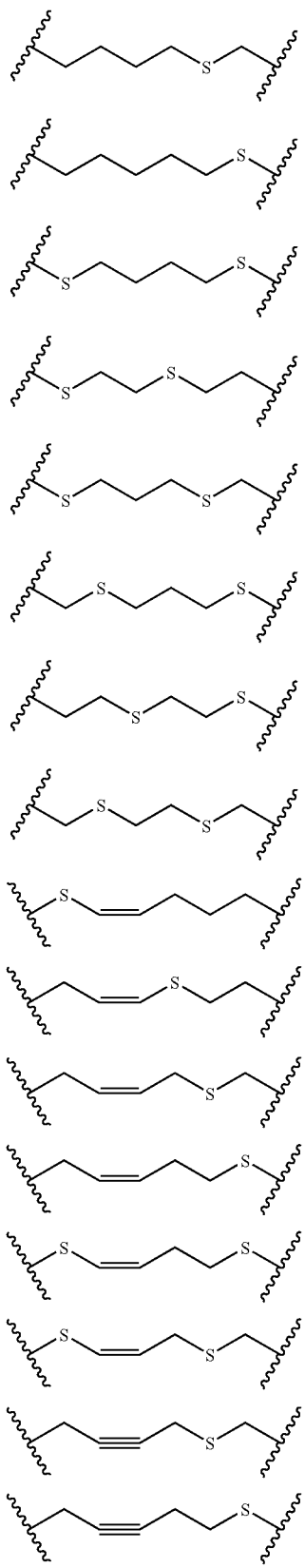

Alternatively, A may be a moiety where O replaces one or two carbon atoms such as one of the following or the like.

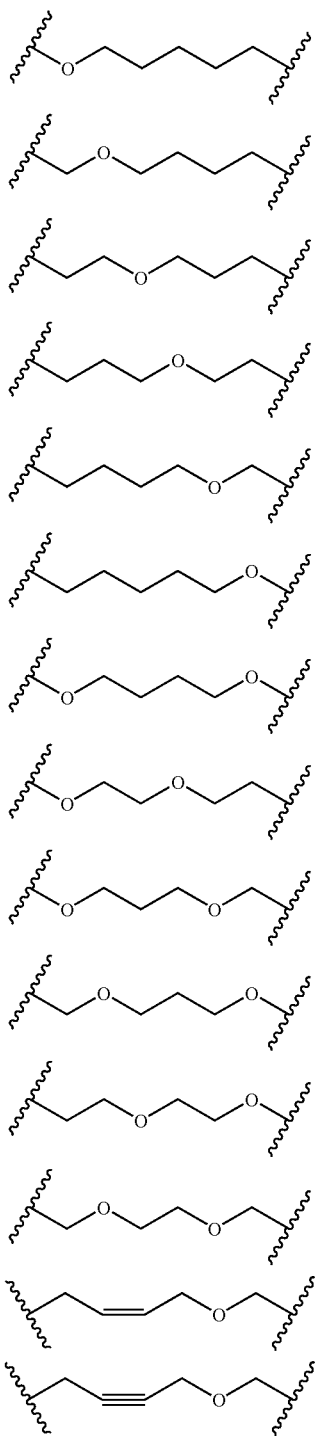

Alternatively, A may have an O replacing one carbon atom and an S replacing another carbon atom, such as one of the following or the like.

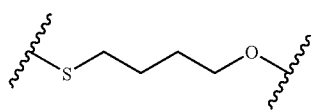

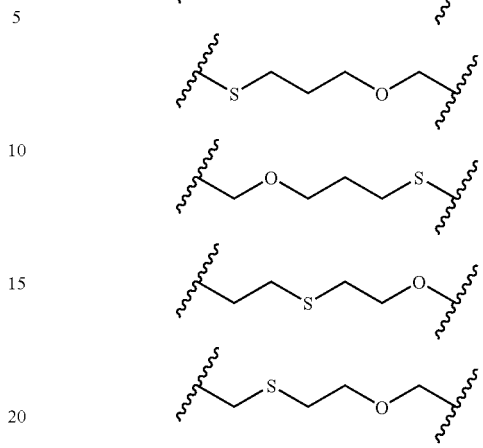

Alternatively, in certain embodiments A is —(CH$_2$)$_m$—Ar—(CH$_2$)$_o$— wherein Ar is interarylene or heterointerarylene, the sum of m and o is 1, 2, 3, or 4, and wherein 1 —CH$_2$— may be replaced by S or O, and 1 —CH$_2$—CH$_2$— may be replaced by —CH═CH— or —C≡C—. In other words, in one embodiment A comprises:
1) a) 1, 2, 3, or 4 —CH$_2$— moieties, or
   b) 0, 1 or 2 —CH$_2$— moieties and —CH═CH— or —C≡C—; and
2) Ar;

e.g. —CH$_2$—Ar—, —(CH$_2$)$_2$—Ar—, —CH═CH—Ar—, —C≡C—Ar—, —CH$_2$—Ar—CH$_2$—, —CH$_2$Ar—(CH$_2$)$_2$—, —CH$_2$Ar—CH═CH—, —CH$_2$Ar—C≡C—, —(CH$_2$)$_2$—Ar—(CH$_2$)$_2$—, and the like;

in another embodiment A comprises:
1) a) O; and 0, 1, 2, or 3 —CH$_2$— moieties; or
   b) O; and 0 or 1 —CH$_2$— moieties and —CH═CH— or —C≡C—; and
2) Ar;

e.g., —O—Ar—, —Ar—CH$_2$—O—, —O—Ar—(CH$_2$)$_2$—, —OAr—CH═CH—, —O—Ar—C≡C—, —O—CH$_2$—Ar—, —O—CH$_2$—Ar—(CH$_2$)$_2$, —O—CH$_2$Ar—CH═CH—, —O—CH$_2$Ar—C≡C—, and the like; or in another embodiment A comprises:
1) a) S; and 0, 1, 2, or 3 —CH$_2$— moieties; or
   b) S; and 0 or 1 —CH$_2$— moieties and —CH═CH— or —C≡C—; and
2) Ar;

e.g., —S—Ar—, —Ar—CH$_2$—S—, —S—Ar—(CH$_2$)$_2$—, —SAr—CH═CH—, —S—Ar—C≡C—, —S—CH$_2$—Ar—, —S—CH$_2$—Ar—(CH$_2$)$_2$, —S—CH$_2$Ar—CH═CH—, —S—CH$_2$Ar—C≡C—, and the like.

In another embodiment, the sum of m and o is 2, 3, or 4 wherein one CH$_2$ may be replaced with S or O and 1 —CH$_2$—CH$_2$— may be replaced by —CH═CH— or —C≡C—.

In another embodiment, the sum of m and o is 3 wherein one CH$_2$ may be replaced with S or O and 1 —CH$_2$—CH$_2$— may be replaced by —CH═CH— or —C≡C—.

In another embodiment, the sum of m and o is 2 wherein one CH$_2$ may be replaced with S or O or 1 —CH$_2$—CH$_2$— may be replaced by —CH═CH— or —C≡C—.

In another embodiment, the sum of m and o is 4 wherein one $CH_2$ may be replaced with S or O and 1 —$CH_2$—$CH_2$— may be replaced by —CH=CH— or —C≡C—.

Interarylene or heterointerarylene refers to aryl or heteroaryl (as defined for B below) which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —$(CH_2)_2$—Ph—.

Substitutents of Ar each have from 0 to 4 carbon atoms, from 0 to 3 oxygen atoms, from 0 to 2 sulfur atoms, from 0 to 2 nitrogen atoms, from 0 to 3 fluorine atoms, from 0 to 1 chlorine atoms, from 0 to 1 bromine atoms, from 0 to 1 iodine atoms, from 0 to 11 hydrogen atoms, and consist of 1 or more of the following components, either alone or in combination: hydrocarbyl, H, —OH, —SH, —O—, —S—, —F, —Cl, —Br, —I, —C≡N, —$CF_3$, —$NO_2$,

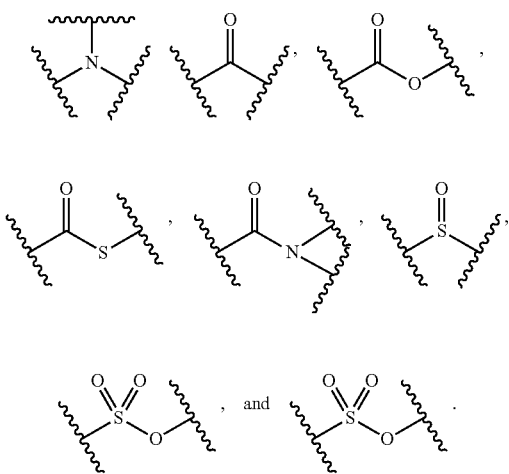

Thus, the substituent may consist of 1 of the components above, such as hydrocarbyl, H, —F, —Cl, —Br, —I, —OH, —SH, —C≡N, —$CF_3$, —$NO_2$, —$CO_2H$, etc.

Alternatively, the substituent may consist of 2 of the components above, such as: hydrocarbyl-OH, including alkyl-OH, hydrocarbyl-SH, —O-hydrocarbyl, including O-alkyl, —NH-alkyl, —N(alkyl)$_2$, —$CO_2$-alkyl, —CO-NHalkyl, CO—N(alkyl)$_2$, alkyl-CN, etc.

If a group is asymmetrical, it can be oriented in any direction possible. For example,

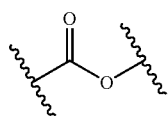 [SMILES: *OC(*)=O]

allows the group to be oriented as shown, or oriented as

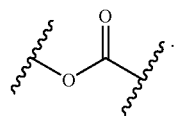

Thus, using this example, Ar could be one of the two structures shown below.

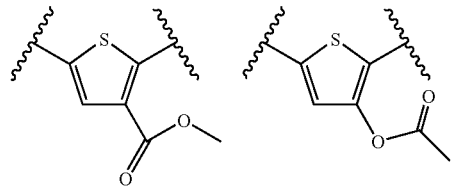 [SMILES: *c1cc(C(=O)OC)c(*)s1 ; *c1cc(OC(C)=O)c(*)s1]

Alternatively, the substituent may consist of 3 of the components above, such as: hydrocarbyl-O-hydrocarbyl, alkyl-CO-alkyl, —O-alkyl-$CO_2$, etc.

Alternatively, the substituent may consist of more than 3 of the components above, provided that the other parameters described are met.

In addition to the atoms listed above, a substituent may also have a metal cation or any other stable cation having an atom not listed above if the substituent is acidic and the salt form is stable. For example, —OH may form an —O⁻Na⁺ salt or $CO_2H$ may form a $CO_2^-K^+$ salt. Any cation of the salt is not counted the limitations listed above for the substituents of Ar.

In one embodiment, each substitutent of Ar has from 0 to 4 carbon atoms, from 0 to 3 oxygen atoms, from 0 to 2 sulfur atoms, from 0 to 2 nitrogen atoms, and from 0 to 11 hydrogen atoms, or the substituent is —F, —Cl, —Br, —I, or $CF_3$.

Ar may have as many substituents as the ring will bear.

In one embodiment Ar has 0, 1, or 2, substituents.

In another embodiment Ar has 0 or 1 substituent.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —$(CH_2)_2$—Ph—.

In another embodiment A is —$CH_2$—Ar—$OCH_2$—. In another embodiment A is —$CH_2$—Ph—$OCH_2$—. In another embodiment, Ph is attached at the 1 and 3 positions, otherwise known as m-interphenylene, such as when A has the structure shown below.

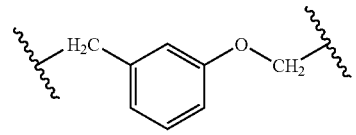 [SMILES: *COc1cccc(C*)c1]

In another embodiment A is —$(CH_2)_6$—, cis —$CH_2CH=CH$—$(CH_2)_3$—, or —$CH_2C≡C$—$(CH_2)3$—, wherein 1 or 2 carbon atoms may be replaced with S or O; or A is —$(CH_2)_2$—Ph— wherein one —$CH_2$— may be replaced with S or O.

In another embodiment A is —$(CH_2)_6$—, cis-$CH_2CH=CH$—$(CH_2)_3$—, or —$CH_2C≡C$—$(CH_2)_3$—, wherein 1 or 2 carbon atoms may be replaced with S or O; or A is —$(CH_2)_2$—Ph—.

In one embodiment, Ar is thienyl.

In other embodiments, A has one of the following structures.

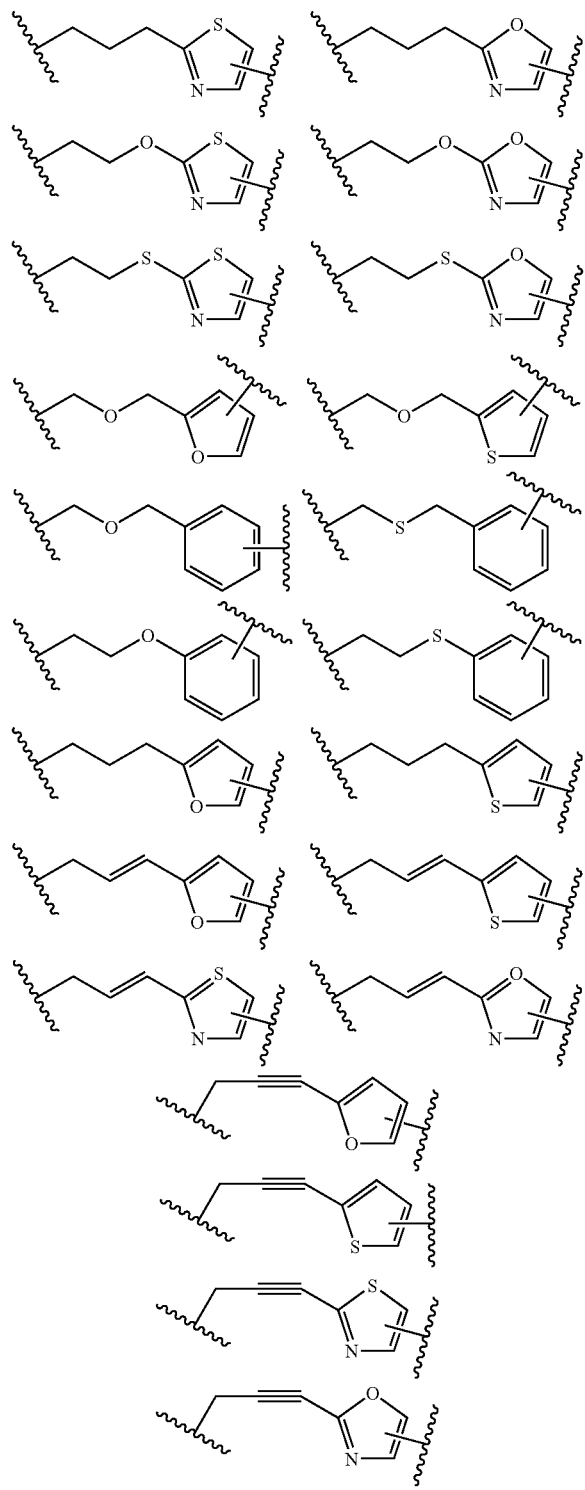

In another embodiment A is —CH₂OCH₂Ar—.
In another embodiment A is —CH₂SCH₂Ar—.
In another embodiment A is —(CH₂)₃Ar—.
In another embodiment A is —CH₂O(CH₂)₄—.
In another embodiment A is —CH₂S(CH₂)₄—.
In another embodiment A is —(CH₂)₆—.

In another embodiment A is cis —CH₂CH=CH—(CH₂)₃—.
In another embodiment A is —CH₂C≡C—(CH₂)₃—.
In another embodiment A is —S(CH₂)₃S(CH₂)₂—.
In another embodiment A is —(CH₂)₄OCH₂—.
In another embodiment A is cis —CH₂CH=CH—CH₂OCH₂—.
In another embodiment A is —CH₂CH≡CH—CH₂OCH₂—.
In another embodiment A is —(CH₂)₂S(CH₂)₃—.
In another embodiment A is —CH₂—Ph—OCH₂—, wherein Ph is interphenylene.
In another embodiment A is —CH₂—mPh—OCH₂—, wherein mPh is m-interphenylene.
In another embodiment A is —CH₂—O—(CH₂)₄—.
In another embodiment A is —CH₂—O—CH₂—Ar—, wherein Ar is 2,5-interthienylene.
In another embodiment A is —CH₂—O—CH₂—Ar—, wherein Ar is 2,5-interfurylene.
In another embodiment A is (3-methylphenoxy)methyl.
In another embodiment A is (4-but-2-ynyloxy)methyl.
In another embodiment A is 2-(2-ethylthio)thiazol-4-yl.
In another embodiment A is 2-(3-propyl)thiazol-5-yl.
In another embodiment A is 3-(methoxymethyl)phenyl.
In another embodiment A is 3-(3-propylphenyl).
In another embodiment A is 3-methylphenethyl.
In another embodiment A is 4-(2-ethyl)phenyl.
In another embodiment A is 4-phenethyl.
In another embodiment A is 4-methoxybutyl.
In another embodiment A is 5-(methoxymethyl)furan-2-yl.
In another embodiment A is 5-(methoxymethyl)thiophen-2-yl.
In another embodiment A is 5-(3-propyl)furan-2-yl.
In another embodiment A is 5-(3-propyl)thiophen-2-yl.
In another embodiment A is 6-hexyl.
In another embodiment A is (Z)-6-hex-4-enyl.
In one embodiment A is —(CH₂)$_m$—Ph—(CH₂)$_o$— wherein the sum of m and o is 1, 2, or 3, and wherein one CH₂ may be replaced with S or O.

J is hydrogen, OH, O, SH, S, $C_{1-6}$ alkyl, —O—($C_{1-6}$ alkyl), —S—($C_{1-6}$ alkyl), F, Cl, Br, I, CN, or CF₃.
In one embodiment, J is OH.
In another embodiment, J is O, meaning that the compounds have the formula:

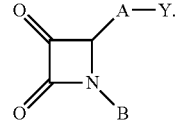

In another embodiment, J is SH.
In another embodiment, J is S, meaning that the compounds have the formula:

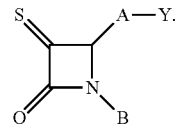

In another embodiment, J is $C_{1-6}$ alkyl.
In another embodiment, J is —O—($C_{1-6}$alkyl).
In another embodiment, J is —S—($C_{1-6}$ alkyl).

For example, in the cases where J is $C_{1-6}$ alkyl, —O—($C_{1-6}$ alkyl), or —S—($C_{1-6}$ alkyl), the C1-6 alkyl could be methyl, ethyl, propyl, isopropyl, one of the butyl isomers, one of the pentyl isomers, one of the hexyl isomers, or cyclopropyl, cyclobutyl, cyclopentyl, or cyclohexyl.

In another embodiment, J is F.
In another embodiment, J is Cl.
In another embodiment, J is Br.
In another embodiment, J is I.
In another embodiment, J is CN.
In another embodiment, J is $CF_3$.
In another embodiment, J is hydrogen.

B is aryl or heteroaryl.

Aryl is an aromatic ring or ring system such as phenyl, naphthyl, biphenyl, and the like.

Heteroaryl is aryl having one or more N, O, or S atoms in the ring, i.e. one or more ring carbons are substituted by N, O, and/or S. While not intending to be limiting, examples of heteroaryl include thienyl, pyridinyl, furyl, benzothienyl, benzofuryl, imidizololyl, indolyl, and the like.

Aryl or heteroaryl may be substituted or unsubstituted. Each substituent of aryl or heteroaryl may have from 0 to 12 carbon atoms, from 0 to 4 oxygen atoms, from 0 to 4 sulfur atoms, from 0 to 2 nitrogen atoms, from 0 to 7 fluorine atoms, from 0 to 1 chlorine atoms, from 0 to 1 bromine atoms, from 0 to 1 iodine atoms, from 0 to 27 hydrogen atoms, and consist of 1 or more of the following components, either alone or in combination: hydrocarbyl, H, —OH, —SH, —O—, —S—, —F, —Cl, —Br, —I, —C≡N, —$CF_3$, —$NO_2$,

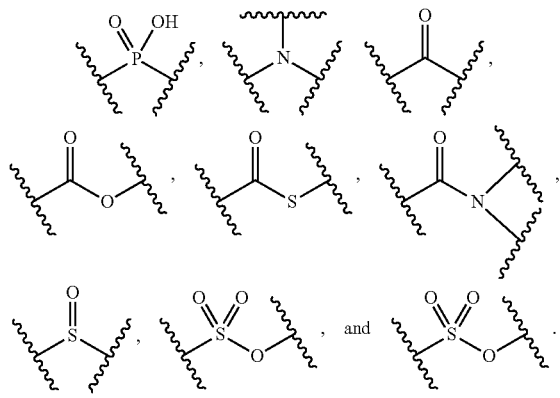

As explained, above, the substituent may consist of 1, 2, or 3 or more of these components.

In addition to the atoms listed above, a substituent may also have a metal cation or other stable cation having an atom not listed above if the substituent is acidic and the salt form is stable. For example, —OH may form an —$O^-Na^+$ salt or $CO_2H$ may form a $CO_2^-K^+$ salt.

In one embodiment, each substituent has from 0 to 12 carbon atoms, from 0 to 4 oxygen atoms, from 0 to 4 sulfur atoms, from 0 to 2 nitrogen atoms, and from 0 to 27 hydrogen atoms, or the substituent is —$CF_3$, —F, —Cl, —Br, or —I.

Examples of Substituents Contemplated for B Include:
a. hydrocarbyl, including alkyl, alkenyl, alkynyl, phenyl, and combinations thereof;
b. hydrocarbyloxy, meaning O-hydrocarbyl such as $OCH_3$, $OCH_2CH_3$, O-cyclohexyl, etc;
   alkoxy is O-alkyl;
   $C_{1-6}$ alkoxy is alkoxy having 1, 2, 3, 4, 5, or 6 carbon atoms;
c. other ether substituents such as $CH_2OCH_3$, $(CH_2)_2OCH(CH_3)_2$, and the like;
d. thioether substituents including S-hydrocarbyl and other thioether substituents;
e. hydroxyhydrocarbyl, meaning hydrocarbyl-OH such as $CH_2OH$, $C(CH_3)_2OH$, etc;
f. nitrogen substituents such as $NO_2$, CN, and the like, including
g. amino, such as $NH_2$, $NH(CH_2CH_3OH)$, $NHCH_3$, and the like;
   $C_{0-6}$ amino is amino having 0, 1, 2, 3, 4, 5 or 6 carbon atoms;
h. carbonyl substituents, such as $CO_2H$, ester, amide, acyl, and the like;
   acyl is —C(O)-hydrocarbyl;
i. halogen, such as chloro, fluoro, bromo, and the like
j. fluorocarbyl, such as $CF_3$, $CF_2CF_3$, etc.;
k. sulfur substituents, including S-hydrocarbyl, SH, $SO_3H$, $SO_2$-hydrocarbyl, $SO_3$-hydrocarbyl, and the like.

Substituted aryl or heteroaryl may have as many substituents as the ring or ring system will bear, and the substituents may be the same or different. Thus, for example, an aryl ring or a heteroaryl ring may be substituted with chloro and methyl; methyl, OH, and F; CN, $NO_2$, and ethyl; and the like including any conceivable substituent or combination of substituent possible in light of this disclosure.

Substituted aryl or substituted heteroaryl also includes a bicyclic or polycyclic ring system wherein one or more rings are aromatic and one or more rings are not. For example, indanonyl, indanyl, indanolyl, tetralonyl, and the like are substituted aryl. For this type of polycyclic ring system, an aromatic or heteroaromatic ring, not a non-aromatic ring, must be attached to the remainder of the molecule, i.e. the part of the molecule that is not B. In other words, in any structure depicting —B herein, where — is a bond, the bond is a direct bond to an aromatic ring.

In one embodiment, B is substituted aryl or heteroaryl.
In another embodiment B is substituted phenyl.
In another embodiment B has no halogen atoms.
In another embodiment B is 4-(1-hydroxy-2,2-dimethylpropyl)phenyl.
In another embodiment B is 4-(1-hydroxy-2-methylpropan-2-yl)phenyl.
In another embodiment B is 4-(1-hydroxy-2-methylpropyl)phenyl.
In another embodiment B is 4-(1-hydroxybutyl)phenyl.
in another embodiment B is 4-(1-hydroxyheptyl)phenyl.
In another embodiment B is 4-(1-hydroxyhexyl)phenyl.
In another embodiment B is 4-(1-hydroxypentyl)phenyl.
In another embodiment B is 4-(1-hydroxypropyl)phenyl.
In another embodiment B is 4-(3-hydroxy-2-methylheptan-2-yl)phenyl.
In another embodiment B is 4-(3-hydroxy-2-methyloctan-2-yl)phenyl.
In another embodiment B is 1-hydroxy-2,3-dihydro-1H-inden-5-yl.
In another embodiment B is 2,3-dihydro-1H-inden-5-yl.
In another embodiment B is 3-(hydroxy(1-propylcyclobutyl)methyl)phenyl.
In another embodiment B is 4-(1-hydroxy-5,5-dimethylhexyl)phenyl.
In another embodiment B is 4-(hydroxy(1-propylcyclobutyl)methyl)phenyl.
In another embodiment B is 4-tert-butylphenyl.
In another embodiment B is 4-hexylphenyl.
In another embodiment B is 4-(1-hydroxy-2-phenylethyl)phenyl.

In another embodiment B is 4-(1-hydroxy-3-phenylpropyl)phenyl.

In another embodiment B is 4-(1-hydroxycyclobutyl)phenyl.

In another embodiment B is 4-(2-cyclohexyl-1-hydroxyethyl)phenyl.

In another embodiment B is 4-(3-cyclohexyl-1-hydroxypropyl)phenyl.

In another embodiment B is 4-(cyclohexyl(hydroxy)methyl)phenyl.

In another embodiment B is 4-(cyclohexylmethyl)phenyl.

In another embodiment B is 4-(hydroxy(phenyl)methyl)phenyl.

In another embodiment, B is phenyl substituted with $C_{1-10}$ acyl. $C_{1-10}$ acyl is acyl having from 1 to 10 carbon atoms.

Some hypothetical examples of useful compounds are shown below.

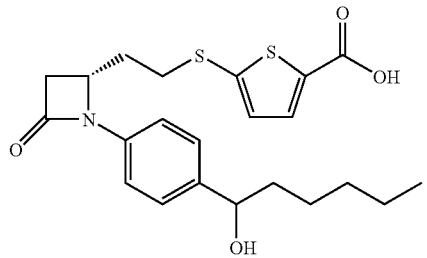

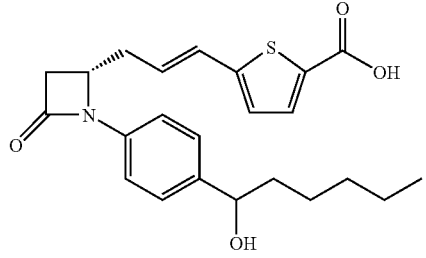

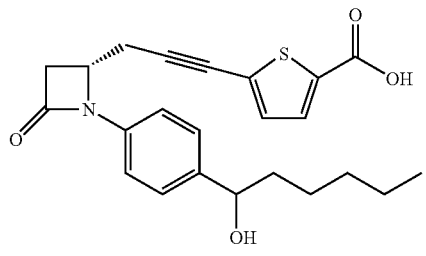

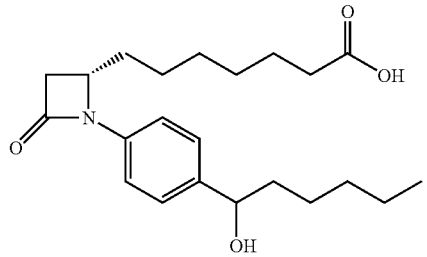

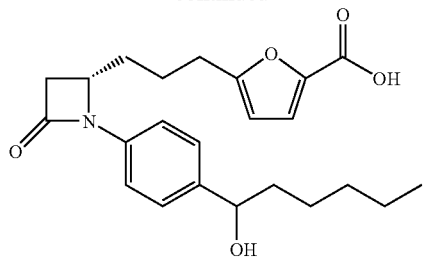

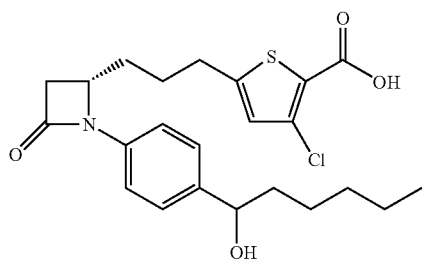

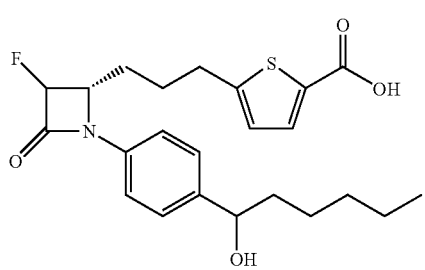

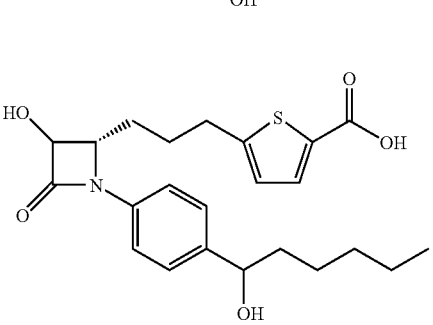

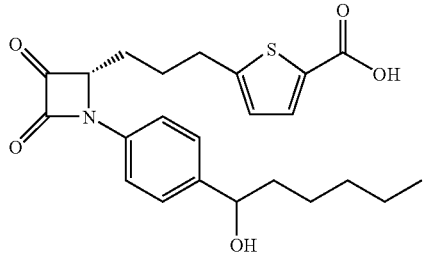

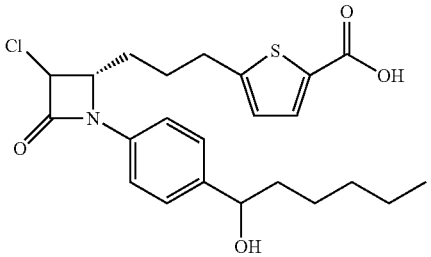

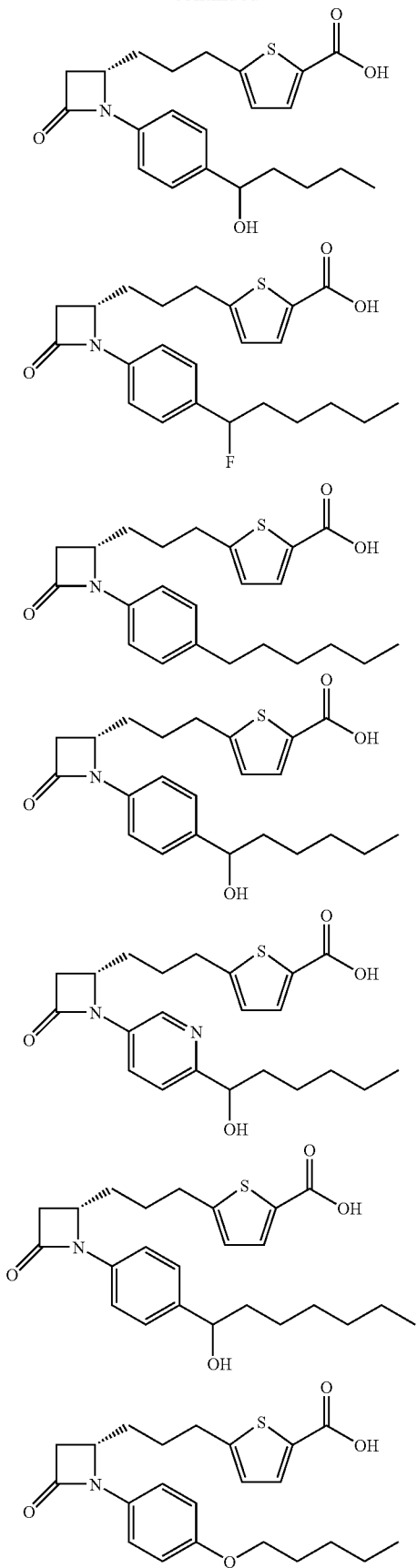
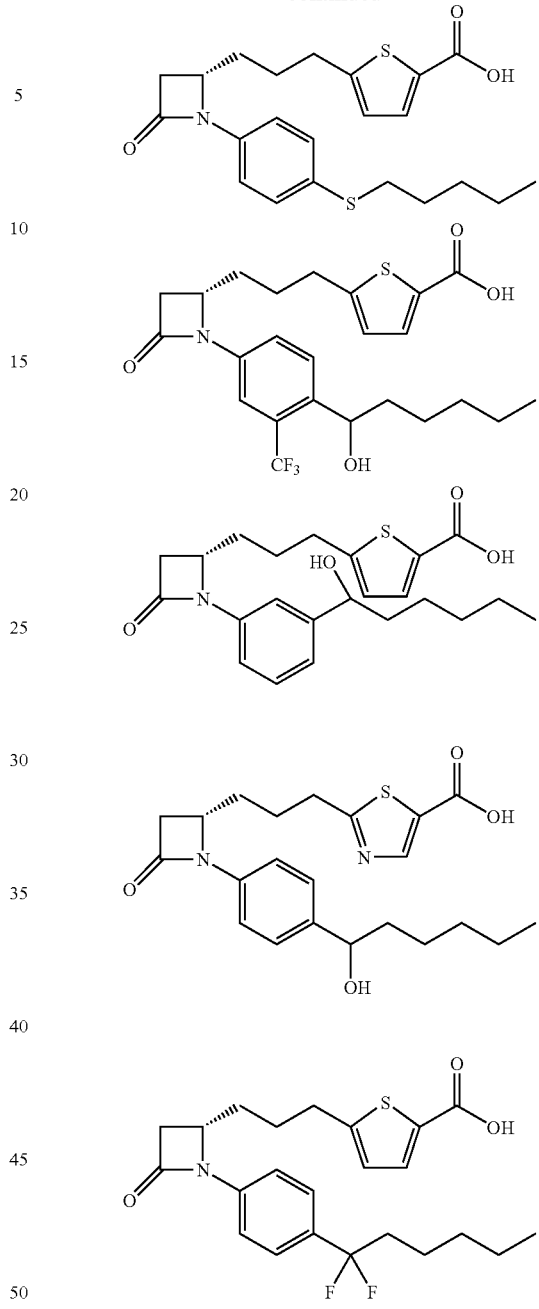
In one embodiment, Y is selected from $CO_2R^2$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$,
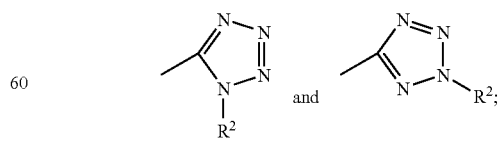
and
wherein $R^2$ is independently H, $C_1$-$C_6$ alkyl, unsubstituted phenyl, or unsubstituted biphenyl.
In another embodiment, B is substituted phenyl.

In another embodiment, the compound is further represented by a structural formula:

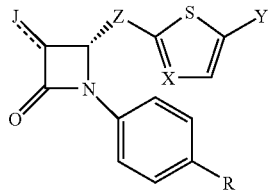

wherein X is CH or N;
Z is —(CH$_2$)$_3$—, —CH=CH—CH$_2$—, —O(CH$_2$)$_2$—, —CH$_2$OCH$_2$—, —(CH$_2$)$_2$O—, —S(CH$_2$)$_2$—, —CH$_2$SCH$_2$—, or —(CH$_2$)$_2$S—; and
R is C$_{4-8}$ alkyl or C$_{4-8}$ hydroxyalkyl.

Hydroxyalkyl is alkyl having a hydroxyl substituent.
C$_{4-8}$ indicates that the moiety has from 4-8 carbon atoms.
In another embodiment, the compound is further represented by a structural formula:

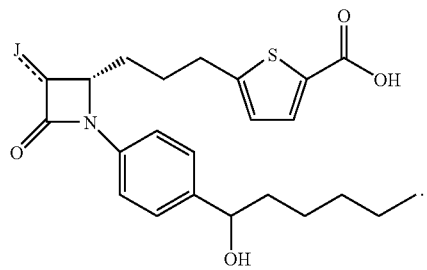

In another embodiment, the compound is further represented by a structural formula:

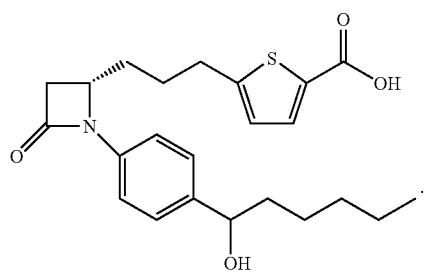 [SMILES: CCCCCC(O)c1ccc(N2C(=O)C[C@@H]2CCCc2ccc(C(=O)O)s2)cc1]

In another embodiment, J is OH.
In another embodiment, J is F.
In another embodiment, J is Cl.
In another embodiment, J is CN.
In another embodiment, J is CF$_3$.
In another embodiment, J is hydrogen.
In another embodiment, B is substituted pyridinyl.
In another embodiment, B is substituted pyridinyl having from 1 to 3 substituents, wherein one substituent is alkyl or hydroxyalkyl having from 3 to 10 carbon atoms, and the other substituents are independently selected from: F, Cl, Br, I, CF$_3$, CH$_3$, OH, OCH$_3$, CN, CH$_2$OH, and NO$_2$.

In another embodiment, B is substituted phenyl having from 1 to 3 substituents, wherein one substituent is alkyl or hydroxyalkyl having from 3 to 10 carbon atoms, and the other substituents are independently selected from: F, Cl, Br, I, CF$_3$, CH$_3$, OH, OCH$_3$, CN, CH$_2$OH, and NO$_2$.

In another embodiment, B is substituted or unsubstituted furyl, thienyl, imidazole, thiazole, or oxazole. In other words each of the furyl, thienyl, imidazole, thiazole, or oxazole may be substituted or unsubstituted.

In another embodiment, the compound is further represented by a structural formula:

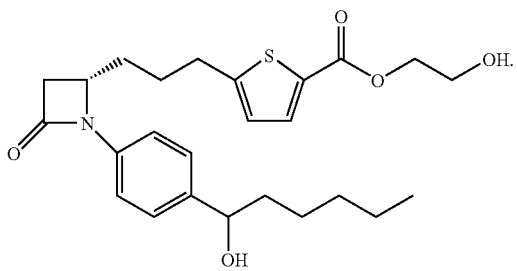 [SMILES: CCCCCC(O)c1ccc(N2C(=O)C[C@@H]2CCCc2ccc(C(=O)OCCO)s2)cc1]

Another embodiment is a method of reducing intraocular pressure comprising administering a therapeutically effective amount of a compound disclosed herein to a mammal in need thereof.

Another embodiment is use of a compound disclosed herein in the manufacture of a medicament for the treatment of glaucoma or ocular hypertension in a mammal.

Another embodiment is a kit comprising a composition comprising compound disclosed herein, a container, and instructions for administration of said composition to a mammal for the treatment of glaucoma or ocular hypertension.

Another embodiment is a composition comprising a compound disclosed herein, wherein said composition is a liquid which is ophthalmically acceptable.

Another embodiment is a method of growing hair or improving the appearance of hair comprising administering a therapeutically effective amount of a compound disclosed herein to a mammal in need thereof.

Another embodiment is use of a compound disclosed herein in the manufacture of a medicament for growing hair or improving the appearance of hair in a mammal.

Synthetic Methods

These compounds may be prepared by adapting the methods disclosed in US Patent Application Publication No. 20070287742. Variation of J may be achieved by a variety of methods. For example, base-catalyzed halogenation of the carbon α- to the carbonyl followed by substitution might be used to obtain the desired substituent.

The procedures below illustrate one of many possible useful methods.

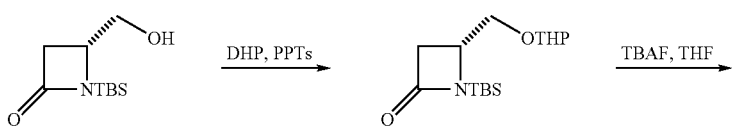

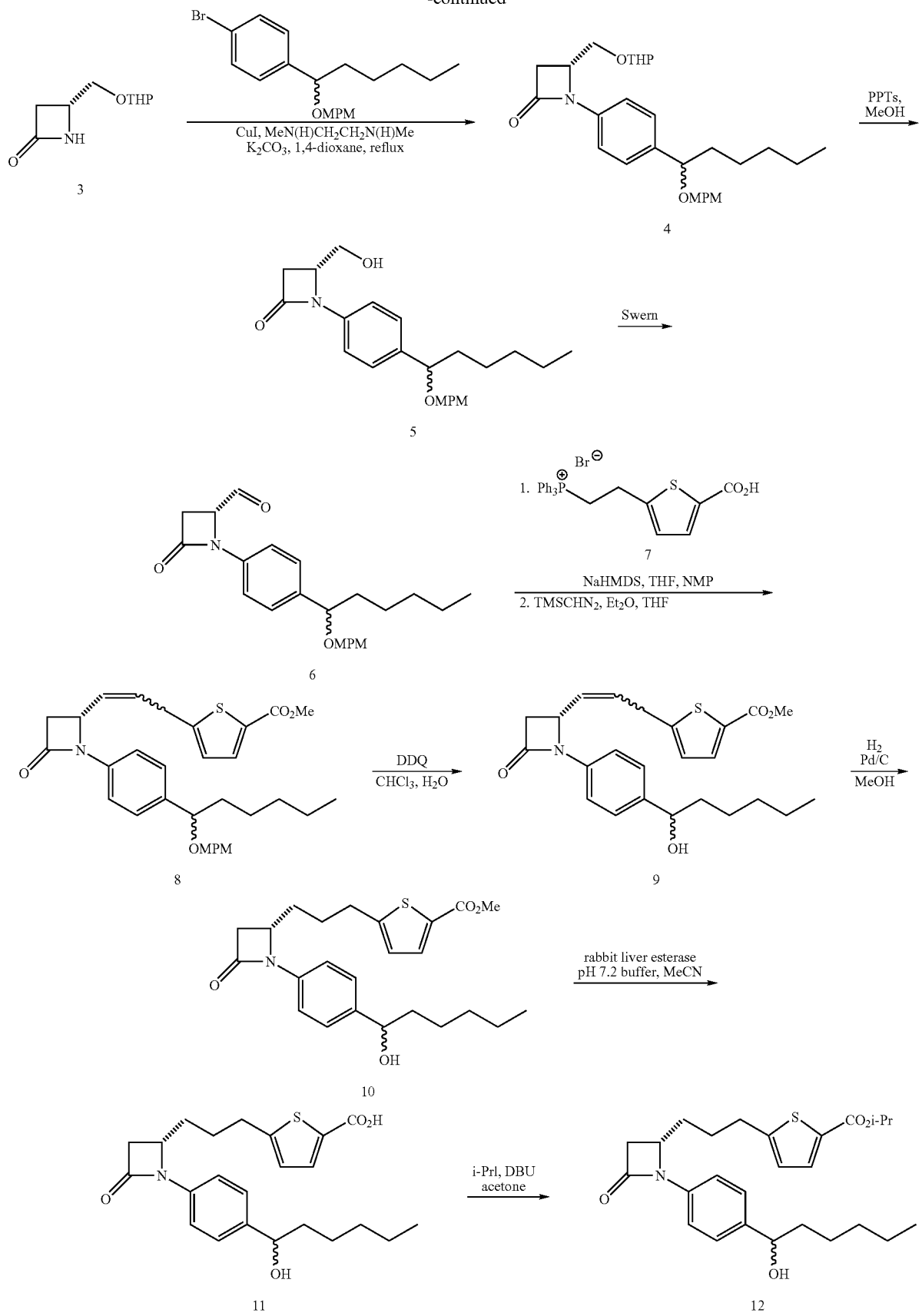

EXAMPLE 1

(5-(3-((2S)-1-(4-(1-hydroxyhexyl)phenyl)-4-oxoazetidin-2-yl)propyl)thiophene-2-carboxylic acid (11)

Step 1. Protection of 1 to give 2

3,4-Dihydro-2H-pyran (90 µL, 0.99 mmol) and pyridinium p-toluenesulfonate (PPTs, 12 mg, 0.048 mmol) were added to a solution of (R)-1-(tert-butyldimethylsilyl)-4-(hydroxymethyl)azetidin-2-one (1, for representative preparation see Tetrahedron Lett. 1998, 5125-5128, 101 mg, 0.47 mmol) in $CH_2Cl_2$ (2.0 mL). After 18 h at room temperature, the reaction mixture was concentrated to dryness. Purification of the crude residue by flash chromatography on silica gel (50% EtOAc/hexanes) afforded 125 mg (89%) of 2.

Step 2. Deprotection of 2 to give 3

Tetrabutylammonium fluoride (10.0 mL of a 1.0 M solution in THF, 10.0 mmol) was added to a solution of 2 (900 mg, 3.0 mmol) in THF (20 mL) at 0° C. and the mixture was allowed to warm to room temperature. After 18 h, the mixture was concentrated in vacuo. Water (50 mL) was added and the mixture was extracted with EtOAc (3×75 mL). The combined organic phase was washed with brine (50 mL) then dried ($Na_2SO_4$), filtered and concentrated in vacuo. Purification of the crude residue on 80 g silica gel (50% EtOAc/hexanes→EtOAc, gradient) afforded 393 mg (71%) of 3.

Step 3. Arylation of 3 to give 4

Copper (I) iodide (40 mg, 0.21 mmol) and N,N'-dimethylethylenediamine (45 µL, 0.42 mmol) were added in rapid succession to a mixture of 3 (195 mg, 1.05 mmol), racemic 1-bromo-4-(1-(4-methoxybenzyloxy)hexyl)benzene (see Old and Dinh, WO/2006098918, incorporated by reference herein, 396 mg, 1.05 mmol) and potassium carbonate (289 mg, 2.09 mmol) in 1,4-dioxane (2.6 mL). The mixture was heated at reflux. After 48 h, the mixture was cooled to room temperature, diluted with EtOAc (20 mL) and filtered through celite, washing with excess EtOAc. The filtrate was concentrated in vacuo. Purification of the residue by chromatography on 40 g silica gel (hexanes →EtOAc, gradient) afforded 284 mg (56%) of 4 as a mixture of protected alcohol isomers.

Step 4. Deprotection of 4 to give 5

PPTs (15 mg, 0.060 mmol) was added to a solution of 4 (284 mg, 0.59 mmol) in MeOH (5.9 mL) and the mixture was heated at 40° C. After 18 h, the mixture was cooled to room temperature and concentrated in vacuo. Purification of the residue by chromatography on 40 g silica gel (hexanes→EtOAc, gradient) afforded 234 mg (quant.) of 5 as a mixture of protected alcohol isomers.

Step 5. Oxidation of 5 to give 6

DMSO (62 µL, 0.87 mmol) was added to a solution of oxalyl chloride (210 µL of a 2.0 M solution in $CH_2Cl_2$, 0.42 mmol) and $CH_2Cl_2$ (3.0 mL) at −78 ° C. After 15 min, a solution of alcohol 5 (140 mg, 0.35 mmol) in $CH_2Cl_2$ (1.0 mL) was added via cannula. After 15 min, triethylamine (393 µL, 2.82 mmol) was added and the reaction mixture was allowed to 0 ° C. After 1 h at 0 ° C. the mixture was allowed to warm to room temperature. After 30 min at room temperature, the reaction mixture was partitioned between $CH_2Cl_2$ (20 mL) and saturated aqueous $NaHCO_3$ (20 mL). The phases were separated and the aqueous phase was extracted with $CH_2Cl_2$ (2×20 mL). The combined organic phase was dried ($Na_2SO_4$), filtered and concentrated in vacuo to afford the crude aldehyde 6 which was used without further purification.

Step 6. Wittig reaction of 6 with 7, followed by esterification to give 8

A solution of sodium bis(trimethylsilyl)amide (0.71 mL of a 1.0 M solution in THF, 0.71 mmol) was added to a solution of phosphonium salt 7 (see U.S. Provisional Patent Application No. 60/894,267, 176 mg, 0.35 mmol) in 1-methyl-2-pyrrolidinone (NMP, 0.71 mL) at 0° C. After stirring vigorously for 30 min at 0° C., the deep red mixture was cooled to −20° C. and a solution of aldehyde 6 (~0.35 mmol) in THF (0.71 mL) was added via cannula. After 30 min at −20° C. the mixture was allowed to warm to 0° C. After 1 h at 0° C., the reaction was quenched with saturated aqueous $NH_4Cl$ (10 mL) and extracted with EtOAc (3×20 mL). The combined organic phase was washed with brine (20 mL), dried ($Na_2SO_4$), filtered and concentrated in vacuo. The crude material was dissolved in THF (3.5 mL), cooled to 0° C., and treated dropwise with a solution of (trimethylsilyl)diazomethane (0.88 mL of a 2.0 M solution in $Et_2O$, 1.76 mmol). The mixture was allowed to warm to room temperature. After 2 h, the reaction mixture was concentrated in vacuo.

Purification of the crude residue by chromatography on 12 g silica gel (hexanes→50% EtOAc/hexanes→EtOAc, gradient) afforded 33 mg (17% over 3 steps) of ester 8 as a mixture of olefin and protected alcohol isomers.

Step 8. Deprotection of 8 to give 9

2,3-Dichloro-5,6-dicyano-1,4-benzoquinone (DDQ, 15 mg, 0.066 mmol) was added to a mixture of 8 (33 mg, 0.06 mmol) in $CHCl_3$ (0.75 mL) and water (0.05 mL) at 0° C. After 45 min at 0° C., the reaction mixture was allowed to warm to room temperature. After 30 min at room temperature, the reaction was quenched with saturated aqueous $NaHCO_3$ (5 mL). The mixture was extracted with EtOAc (3×15 mL). The combined organic phase was washed with saturated aqueous $NaHSO_3$ (2×10 mL) and brine (10 mL) then dried ($Na_2SO_4$), filtered and concentrated in vacuo. Purification of the crude residue by chromatography on 12 g silica (hexanes→40% EtOAc/hexanes, gradient) afforded 16 mg (62%) alcohol 9 as a mixture of olefin and alcohol isomers.

Step 7. Hydrogenation of 9 to give 10

Palladium on carbon (10 wt. %, 5 mg) was added to a solution of alkene 9 (16 mg, 0.037 mmol) in MeOH (0.75 mL). A hydrogen atmosphere was established by evacuating and refilling with hydrogen (5×) and the mixture was stirred under a balloon of hydrogen. After 18 h, the reaction was diluted with EtOAc filtered through celite, washing with excess EtOAc and MeOH. The filtrate was concentrated in vacuo to afford 14 mg (87%) of 10 as a mixture of alcohol isomers.

Step 8. Saponification of 10 to give 11

Ester 10 (14 mg, 0.033 mmol) was dissolved in MeCN (0.2 mL) and pH 7.2 buffer (4.0 mL) was added. Rabbit liver esterase (80 units/mg, 10 mg, 800 units) was added and the mixture was stirred vigorously at room temperature. After 4 d, the mixture was diluted with MeCN (25 mL) and concentrated to dryness. Purification of the crude residue by chromatography on 4 g silica gel ($CH_2Cl_2$→20% MeOH/$CH_2Cl_2$, gradient) afforded 4 mg (29%) of ester 10 and 7 mg (52%) of the title compound (11) as a mixture of alcohol isomers.

EXAMPLE 2

Isopropyl (5-(3-((2S)-1-(4-(1-hydroxyhexyl)phenyl)-4-oxoazetidin-2-yl)propyl)thiophene-2-carboxylate (12)

1,8-Diazabicyclo[5.4.0]undec-7-ene (DBU, 3.6 µL, 0.024 mmol) and 2-iodopropane (40 □L, 0.40 mmol) were added to a solution of acid 11 (5 mg, 0.012 mmol) in acetone (0.12 mL) at room temperature under nitrogen. After 3 days at room temperature, the solvent was removed under a stream of nitrogen. The residue was diluted with water (1 mL), acidified with 1.0 N HCl (1 mL) and extracted with EtOAc (3×10 mL). The combined organic phase was washed with brine (5 mL), dried ($Na_2SO_4$), filtered and concentrated in vacuo. Purification of the residue by flash column chromatography on 4 g silica (hexanes→50% EtOAc/hexanes, gradient) afforded 4 mg (73%) of the title compound (12) as a mixture of alcohol isomers.

In Vitro Testing

U.S. patent application Ser. No. 11/553,143, filed on Oct. 26, 2006, incorporated by reference herein, describes the methods used to obtain the in vitro data in Table 1 below.

| | EP2 data | | | EP4 data | | Other Receptors (EC50 in nM) | | | | | |
|---|---|---|---|---|---|---|---|---|---|---|---|
| | flipr | cAMP | | flipr | | | | | | | |
| Structure | EC50 | EC50 | Ki | EC50 | KI | hFP | hEPt | hEP3A | hTP | hIP | hDP |
| 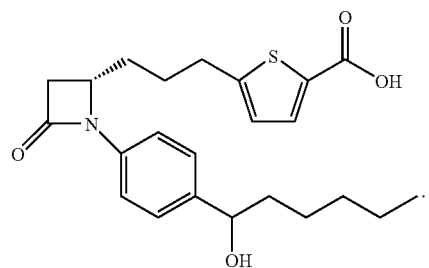 [SMILES: CCCCCC(O)c1ccc(N2C(=O)C[C@@H]2CCCc2ccc(C(=O)O)s2)cc1] | 1.1 | 0.4 | 10 | >10000 | 1453 | NA | NA | 42 | NA | NA | 4736 |

From the methods disclosed herein, a person of ordinary skill in the art can prepare the compounds disclosed herein by using the disclosed methods, by adaptations readily ascertainable by those in the art from the disclosure herein, and/or by the knowledge generally available in the art.

In Vivo Testing

U.S. Pat. No. 7,091,231 describes the methods used to carry out the tests reported below.

Isopropyl (5-(3-((2S)-1-(4-(1-hydroxyhexyl)phenyl)-4-oxoazetidin-2-yl)propyl)thiophene-2-carboxylate (12) was tested in normotensive dogs at 0.01%, dosing once daily for 5 days. The maximum intraocular pressure (IOP) decrease from baseline was 3.7 mmHg (25%) at 6 h; the maximum ocular surface hyperemia (OSH) score was 1.7 at 50 h. This compound was also tested in laser-induced hypertensive monkeys, using one single day dose. At 0.01%, the maximum IOP decrease from baseline was 12.6 mmHg (35%) at 24 h.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

What is claimed is:

1. A compound represented by a structural formula:

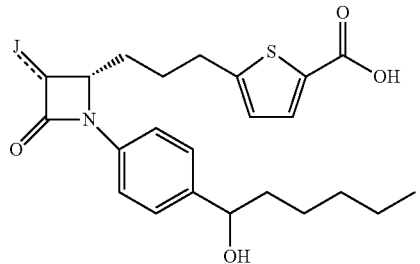

wherein J is hydrogen, OH, O, SH, S, $C_{1-6}$ alkyl, —O—($C_{1-6}$ alkyl), —S—($C_{1-6}$ alkyl), F, Cl, Br, I, CN, or $CF_3$.

2. The compound of claim 1 further represented by a structural formula:

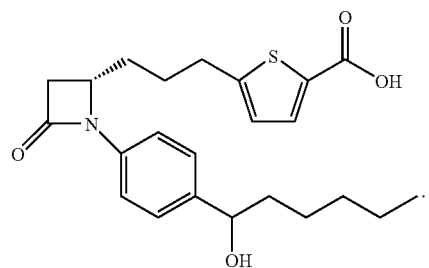 [SMILES: CCCCCC(O)c1ccc(N2C(=O)C[C@@H]2CCCc2ccc(C(=O)O)s2)cc1]

3. A compound represented by a structural formula:

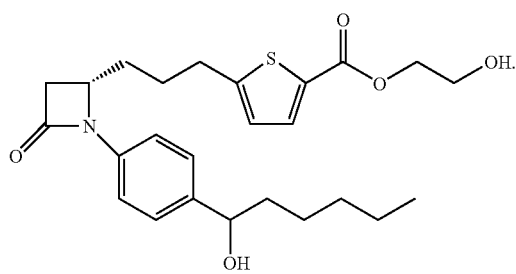 [SMILES: CCCCCC(O)c1ccc(N2C(=O)C[C@@H]2CCCc2ccc(C(=O)OCCO)s2)cc1]

* * * * *

UNITED STATES PATENT AND TRADEMARK OFFICE
CERTIFICATE OF CORRECTION

Page 1 of 2

PATENT NO. : 8,440,819 B2
APPLICATION NO. : 12/372417
DATED : May 14, 2013
INVENTOR(S) : David W. Old It is certified that error appears in the above-identified patent and that said Letters Patent is hereby corrected as shown below:

In the Specification

In column 1, line 38, delete "pupilary" and insert -- pupillary --, therefor.

In column 1, line 53, delete "glaucoma" and insert -- glaucoma. --, therefor.

In column 2, line 27, delete "1 or 2" and insert -- 1 or 2 carbon --, therefor.

In column 4, line 56, delete "akynyl" and insert -- alkynyl. --, therefor.

In column 5, line 33, delete "$R^4,R^5$" and insert -- $R^4$, $R^5$ --, therefor.

In column 6, lines 61-64, after " 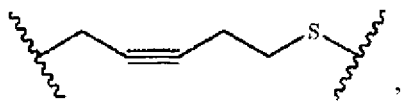 " insert -- . --.

In column 8, line 37, delete "CH$_2$Ar—CH=CH—," and insert -- —CH$_2$Ar—CH=CH—, --, therefor.

In column 9, line 20, delete "Substitutents" and insert -- Substituents --, therefor.

In column 10, line 34, delete "substitutent" and insert -- substituent --, therefor.

In column 11, lines 41-44, delete " 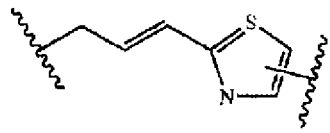 " and insert -- 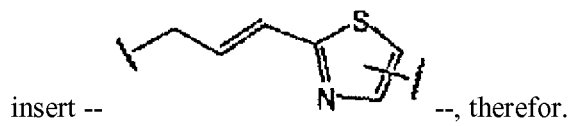 --, therefor.

In column 11, lines 41-44, delete " 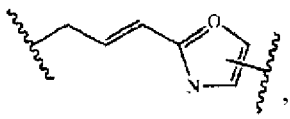 " and insert -- 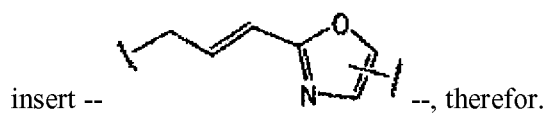 --, therefor.

Signed and Sealed this
Eleventh Day of November, 2014

Michelle K. Lee
*Deputy Director of the United States Patent and Trademark Office*

CERTIFICATE OF CORRECTION (continued)

U.S. Pat. No. 8,440,819 B2

In column 12, line 66, delete "($C_{1-6}$alkyl)." and insert -- ($C_{1-6}$ alkyl). --, therefor.

In column 13, line 2, delete "C1-6" and insert -- $C_{1-6}$ --, therefor.

In column 13, line 21, delete "imidizololyl," and insert -- imidazolyl, --, therefor.

In column 13, line 60, delete "Substituents Contemplated" and insert -- substituents contemplated --, therefor.

In column 14, line 8, after "including" insert -- . --.

In column 14, line 16, after "like" insert -- . --.

In column 23, line 12, delete "$CH_2C1_2$" and insert -- $CH_2Cl_2$ --, therefor.

In column 23, line 32, delete "2.09mmol)" and insert -- 2.09 mmol) --, therefor.

In column 23, line 48, delete "$CH_2C1_2$," and insert -- $CH_2Cl_2$, --, therefor.

In column 23, line 49, delete "$CH_2C1_2$" and insert -- $CH_2Cl_2$ --, therefor.

In column 23, line 50, delete "$CH_2C1_2$" and insert -- $CH_2Cl_2$ --, therefor.

In column 23, line 55, delete "$CH_2C1_2$" and insert -- $CH_2Cl_2$ --, therefor.

In column 23, line 57, delete "$CH_2C1_2$" and insert -- $CH_2Cl_2$ --, therefor.

In column 24, line 15, delete "Step 8." and insert -- Step 7. --, therefor.

In column 24, line 27, delete "Step 7." and insert -- Step 8. --, therefor.

In column 24, line 36, delete "Step 8." and insert -- Step 9. --, therefor.

In column 24, line 53, delete "(40   L," and insert -- (40 μL, --, therefor.